US009456764B2

(12) United States Patent
Burke et al.

(10) Patent No.: US 9,456,764 B2
(45) Date of Patent: Oct. 4, 2016

(54) REDUCING ARTEFACTS IN MRI K-SPACE DATA WITH SIMULTANEOUS RADIATION BEAM INCIDENT ON MRI COLLECTOR COILS

(71) Applicant: Alberta Health Services, Edmonton (CA)

(72) Inventors: Benjamin Burke, Edmonton (CA); B. Gino Fallone, Edmonton (CA); Keith Wachowicz, Edmonton (CA); Satyapal Rathee, Edmonton (CA)

(73) Assignee: Alberta Health Services, Alberta (CA)

( * ) Notice: Subject to any disclaimer, the term of this patent is extended or adjusted under 35 U.S.C. 154(b) by 239 days.

(21) Appl. No.: 14/031,687

(22) Filed: Sep. 19, 2013

(65) Prior Publication Data

US 2015/0080704 A1    Mar. 19, 2015

(51) Int. Cl.
*A61B 5/055* (2006.01)
*G01R 33/565* (2006.01)
*A61N 5/10* (2006.01)
*G01R 33/48* (2006.01)

(52) U.S. Cl.
CPC ............ *A61B 5/055* (2013.01); *A61N 5/1049* (2013.01); *G01R 33/4808* (2013.01); *G01R 33/565* (2013.01); *A61N 2005/1055* (2013.01)

(58) Field of Classification Search
USPC .......................... 324/300–322; 600/407–435; 382/128–131
See application file for complete search history.

(56) References Cited

U.S. PATENT DOCUMENTS

| | | | |
|---|---|---|---|
| 6,173,083 B1 * | 1/2001 | Avinash | 382/260 |
| 6,208,763 B1 * | 3/2001 | Avinash | 382/254 |
| 6,400,151 B1 * | 6/2002 | Haase et al. | 324/309 |
| 6,556,720 B1 * | 4/2003 | Avinash | G01R 33/56563 382/128 |
| 6,757,442 B1 * | 6/2004 | Avinash | 382/274 |
| 7,020,314 B1 * | 3/2006 | Suri | G06K 9/527 382/130 |
| 7,020,343 B1 * | 3/2006 | Avinash | 382/254 |
| 7,206,101 B2 * | 4/2007 | Avinash | 358/3.26 |
| 7,599,579 B2 * | 10/2009 | Avinash | 382/298 |
| 7,778,693 B2 * | 8/2010 | Barbour | A61B 5/0091 600/328 |

(Continued)

*Primary Examiner* — Melissa Koval
*Assistant Examiner* — Tiffany Fetzner
(74) *Attorney, Agent, or Firm* — Dicke, Billig & Czaja, PLLC

(57) ABSTRACT

A computer-implemented method is provided for reducing artifacts in an MRI image as a result of radiation induced current in collector coils of an MRI apparatus. The method comprises the following steps. Selecting a plurality of pixels in a k-space image prior to generation of the MRI image. Analyzing each of the plurality of selected pixels to determine whether a pixel intensity is greater than a predefined global threshold. For each pixel having pixel intensity greater than the predefined global threshold, determining whether the pixel lies within a signal region of the k-space image or outside of the signal region of the k-space image. For each pixel that lies outside of the signal region, modifying the pixel intensity to be similar to a background pixel intensity, thereby creating a modified k-space image. Generating the MRI image based on the modified k-space image. A non-transitory computer readable medium and a radiation therapy system configured to implement the method are also provided.

20 Claims, 8 Drawing Sheets

(56) References Cited

U.S. PATENT DOCUMENTS

| | | | |
|---|---|---|---|
| 8,427,154 B2 * | 4/2013 | Salomir | G01R 33/4804 324/309 |
| 8,552,387 B2 * | 10/2013 | Fenchel | G01T 1/2985 250/363.04 |
| 9,116,219 B1 * | 8/2015 | Posse | G01R 33/5608 |
| 9,271,794 B2 * | 3/2016 | Tyc | A61B 18/22 |
| 2003/0095714 A1 * | 5/2003 | Avinash | 382/260 |
| 2004/0008901 A1 * | 1/2004 | Avinash | 382/260 |
| 2004/0039268 A1 * | 2/2004 | Barbour | A61B 5/0091 600/310 |
| 2010/0166273 A1 * | 7/2010 | Wismuller | G06T 7/0012 382/131 |
| 2011/0248714 A1 * | 10/2011 | Salomir | G01R 33/4804 324/309 |
| 2011/0303835 A1 * | 12/2011 | Fenchel | A61B 6/037 250/252.1 |
| 2015/0080704 A1 * | 3/2015 | Burke et al. | 600/411 |

\* cited by examiner

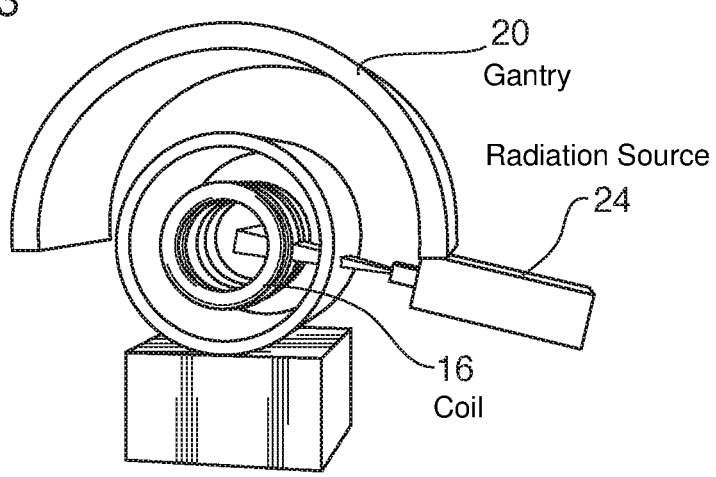

MRI image with a radiation treatment beam inactive

MRI image with a radiation treatment beam active

MRI image with a radiation treatment beam inactive

MRI image with a radiation treatment beam active

Fig. 6   k-space image obtained with radiation treatment beam inactive
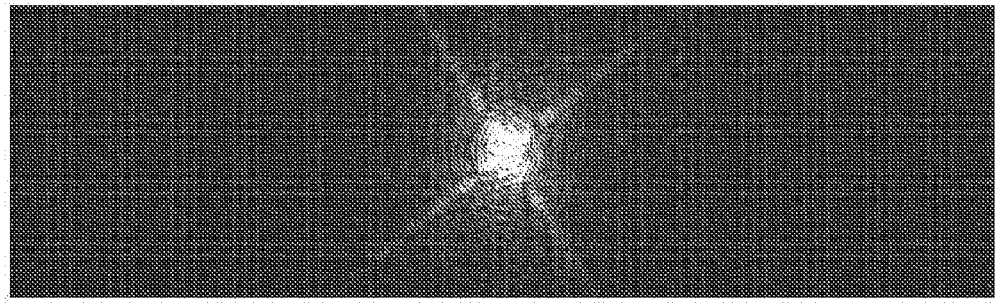
Fig. 7   k-space image obtained with MR imaging repetition time of 300 ms
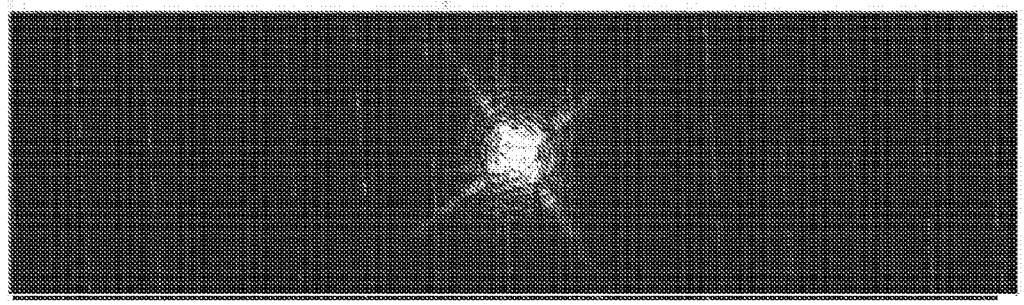
Fig. 8   k-space image obtained with MR imaging repetition time of 300.1 ms
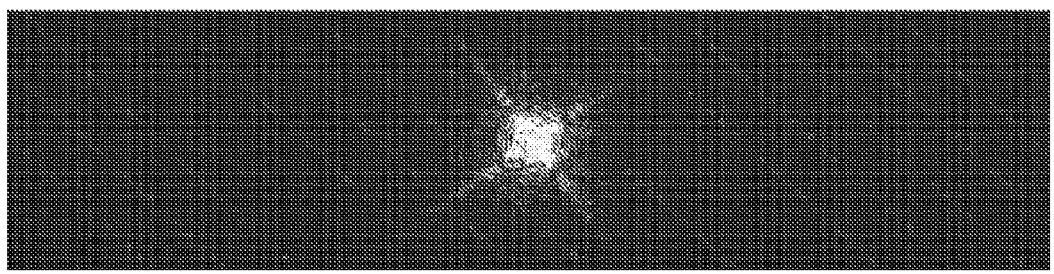

Fig. 9   k-space image obtained with MR imaging repetition time of 301 ms
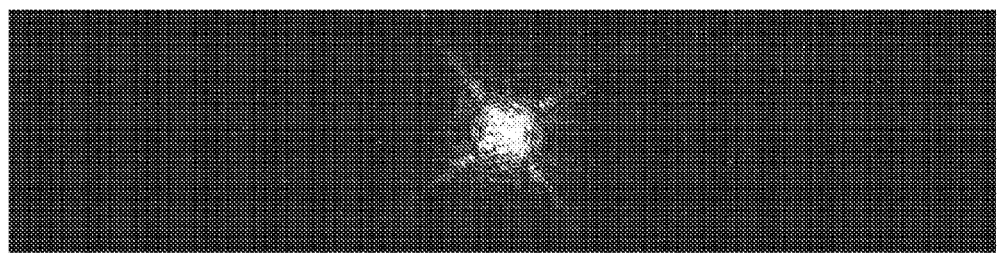
Fig. 10a   k-space image before processing
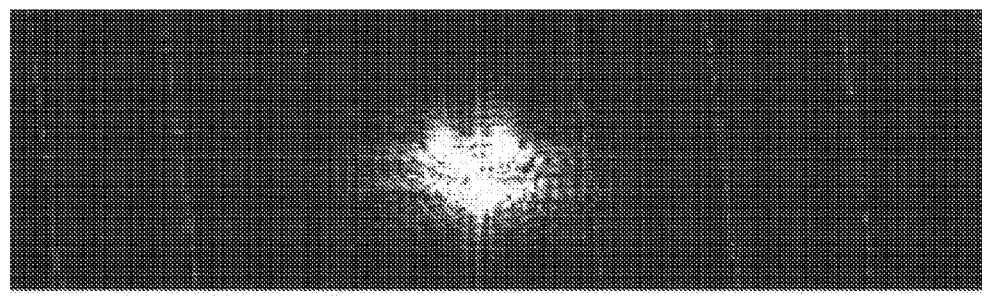
Fig. 10b   k-space image after processing
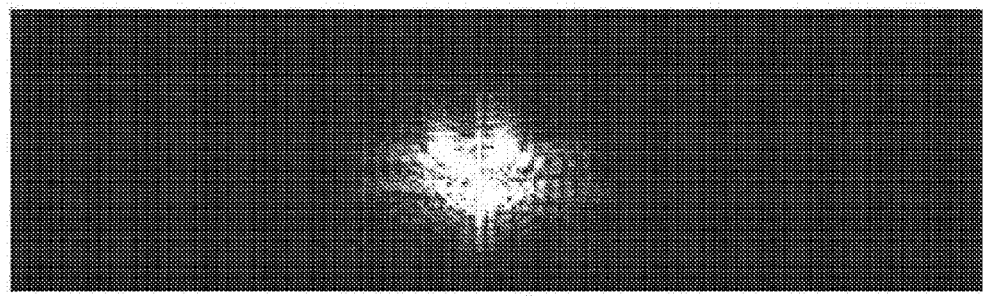

REDUCING ARTEFACTS IN MRI K-SPACE DATA WITH SIMULTANEOUS RADIATION BEAM INCIDENT ON MRI COLLECTOR COILS

The present application relates generally to radiation therapy system and in particular to a radiation therapy system and method for reducing artefacts in MRI images as a result of radiation induced current.

BACKGROUND

Image guidance for radiation therapy is an active area of investigation and technology development. Current radiotherapy practice utilizes highly conformal radiation portals that are directed at a precisely defined target region. It is desirable to provide an imaging method to assist in the placement of the radiation beam at the time of treatment. This technique is known as Image Guided Radiation Therapy (IGRT).

Commercially available techniques for IGRT typically use x-ray or ultrasound imaging technology to produce planar x-ray, computed tomography, or 3D ultrasound images. However, IGRT techniques based on x-rays or ultrasound are not ideally suited to IGRT. For example, x-rays suffer from low soft tissue contrast and are not ideally suited to imaging tumours. X-ray based techniques also use ionizing radiation and result in supplemental dose delivered to the patient. Ultrasound cannot be utilized in all locations of the body. Both x-ray and ultrasound based IGRT techniques are difficult to integrate with a linear accelerator such that they can provide real-time images in any imaging plane during treatment. Yet further, fiducial markers are used in conjunction with these imaging techniques. However, fiducial markers must be placed using an invasive technique, and are thus less desirable.

In order to overcome these deficiencies, it has been proposed to integrate a radiotherapy system with a Magnetic Resonance Imaging (MRI) device. For example, PCT Patent Application Publication No. WO 2007/045076 to Fallone et al., assigned to the assignee of the present application describes a medical linear accelerator (linac) that is combined with a bi-planar permanent magnet suitable for MRI.

An MRI device functions by providing a strong and homogeneous magnetic field that aligns the nuclear magnetic moments of target nuclei. For example, hydrogen nuclei (protons) are the most common imaging target in MRI. In the presence of the magnetic field, the magnetic moments of the nuclei align with the homogeneous magnetic field and oscillate at a frequency determined by the field strength, known as the Larmor frequency. This alignment can be perturbed using a radiofrequency (RF) pulse, such that the magnetization flips from being aligned with the direction of the magnetic field (B0 field) towards being perpendicular to the direction of the magnetic field and thus exhibits transverse magnetization. After the pulse, when the nuclei revert back to their aligned state, the transverse magnetic moment decays to zero, and the longitudinal magnetic moment increases to its original value. Different soft tissues exhibit different transverse and longitudinal relaxation times.

A specific magnetic field is applied across the patient utilizing gradient magnetic coils, and images of the patient can be formed by first generating a specific sequence of perturbing RF pulses and then analyzing the signals that are emitted by the nuclei as they return to their original magnetization state after being perturbed by the RF pulses. RF detector coils receive the emitted RF signals to provide MRI raw data.

However, the quality of an MRI image output by the MRI device may be affected by a pulsed treatment beam from the linac that is incident on the RF detector coils used to detect the RF signals that are generated while nuclei are relaxing after an exciting RF pulse. The incident radiation induces effects in the RF detector coils. An example of the radiation induced effects is a radiation induced current in the detector coil. Radiation induced current can interfere with the fidelity of imaging signals received by the detector coils. This problem manifests itself because, when irradiated with high-energy (megavoltage) photons, the high-energy electrons produced in Compton interactions are likely to escape the thin detector coil material, such as copper strips known to be used in MRI RF detector coils. If there is no influx of electrons to balance this effect, a net positive charge is created in the material. Therefore, if the coil material is part of an electrical circuit, a current induced by the radiation will begin to flow in order to neutralize this charge imbalance.

Since MRI imaging involves forming images based on current induced by RF signals in RF detector coils, radiation induced current in the MRI RF detector coils from an incident treatment beam can introduce artefacts thereby reducing the MRI signal to noise ratio (SNR). While it is possible to time the image acquisition process and the pulsing of radiation so that a radiation pulse is not emitted at the exact same time as the MRI detector coils are receiving RF signals for imaging, such a restriction can limit the adaptability of the system. It would be advantageous to be able to irradiate while imaging.

U.S. patent application Ser. No. 13/253,589 to Rathee et al., which is incorporated entirely herein by reference, is directed to a radiation therapy system comprising a radiation source of generating a beam of radiation, a magnetic resonance imaging (MRI) apparatus comprising at least one detector coil, and an electrically grounded dielectric material between the radiation source and the radiofrequency detector coil for shielding the at least one radiofrequency detector coil from the beam of radiation. Shielding the RF detector coil from the beam of radiation with an electrically grounded dielectric material significantly reduces the radiation induced current in the at least one radiofrequency detector coil, and therefore significantly reduces the amount of radiation induced noise in the MRI images due to radiation.

U.S. Patent Application Publication No. 2011/0087090 to Boernert et al. is directed to a radiation therapy system comprising a radiation therapy subsystem configured to perform radiation therapy by applying radiation pulses to a region of a subject at pulse intervals; a magnetic resonance (MR) imaging subsystem configured to acquire a dataset of MR imaging data samples from the region of the subject over one or more MR sampling intervals that are longer than the pulse intervals, the one or more MR sampling intervals overlapping at least some of the pulse intervals; a synchronizer configured to identify MR imaging data samples of the data set whose acquisition times overlap pulse intervals; and a reconstruction processor configured to reconstruct the dataset, without the measured values for the MR imaging data samples identified as having acquisition times overlapping pulse intervals, to generate a reconstructed MR image. The system requires a synchronizer to ascertain the radiation pulses that overlap with the MR sampling intervals in order to reconstruct the MR imaging data affected by the radiations pulses.

Accordingly, it is desired to provide an alternate method for reducing the deleterious effect of radiation induced current from a linac treatment beam incident on RF detector coils of an MRI device.

SUMMARY

According to an aspect of an embodiment of the invention, there is provided a radiation therapy system comprising a radiation source capable of generating a beam of radiation; a magnetic resonance imaging (MRI) apparatus capable of acquiring image data; and processing structure configured to process the acquired image data to at least reduce artefacts that may be caused during acquisition of the image data by the beam of radiation.

According to another aspect, there is provided a computer-implemented method for reducing artefacts in an MRI image as a result of radiation induced current in collector coils of an MRI apparatus, the method comprising: selecting a plurality of pixels in a k-space image prior to generation of the MRI image; analysing each of the plurality of selected pixels to determine whether a pixel intensity is greater than a predefined global threshold; for each pixel having pixel intensity greater than the predefined global threshold, determining whether the pixel lies within a signal region of the k-space image or outside of the signal region of the k-space image; for each pixel that lies outside of the signal region, modifying the pixel intensity to be similar to a background pixel intensity, thereby creating a modified k-space image; and generating the MRI image based on the modified k-space image According to another aspect, there is provided a non-transitory computer-readable medium having stored thereon instructions for reducing artefacts in an MRI image as a result of radiation induced current in collector coils of an MRI apparatus, the instructions when executed by a processor cause the processor to: select a plurality of pixels in a k-space image prior to generation of the MRI image; analyse each of the plurality of selected pixels to determine whether a pixel intensity is greater than a predefined global threshold; for each pixel having pixel intensity greater than the predefined global threshold, determine whether the pixel lies within a signal region of the k-space image or outside of the signal region of the k-space image; for each pixel that lies outside of the signal region, modify the pixel intensity to be similar to a background pixel intensity, thereby creating a modified k-space image; and generate the MRI image based on the modified k-space image.

According to another aspect, there is provided a radiation therapy system comprising: a radiation source configured to generate a radiation treatment beam; a magnetic resonance imaging (MRI) apparatus configured to acquire image data; and processing structure configured to process the acquired image data to reduce artefacts in an MRI image caused by the radiation treatment beam; the processing structure comprising a processor and memory for storing instructions which, when executed, cause the processor to: select a plurality of pixels in a k-space image prior to generation of the MRI image; analyse each of the plurality of selected pixels to determine whether a pixel intensity is greater than a predefined global threshold; for each pixel having pixel intensity greater than the predefined global threshold, determine whether the pixel lies within a signal region of the k-space image or outside of the signal region of the k-space image; for each pixel that lies outside of the signal region, modify the pixel intensity to be similar to a background pixel intensity, thereby creating a modified k-space image; and generate the MRI image based on the modified k-space image.

BRIEF DESCRIPTION OF THE DRAWINGS

Embodiments will now be described by way of example only with reference to the accompanying drawings in which:

FIG. 3 is a schematic view of a radiation treatment beam incident on an MRI RF coil;

FIG. 6 is a k-space image obtained with a radiation treatment beam inactive;

FIG. 7 is a k-space image obtained with an MR imaging repetition time of 300 ms;

FIG. 8 is a k-space image obtained with an MR imaging repetition time of 300.1 ms;

FIG. 9 is a k-space image obtained with an MR imaging repetition time of 301 ms;

FIGS. 10a and 10b are k-space images before and after processing of k-space image data, respectively;

DETAILED DESCRIPTION OF THE EMBODIMENTS

Figure 1:
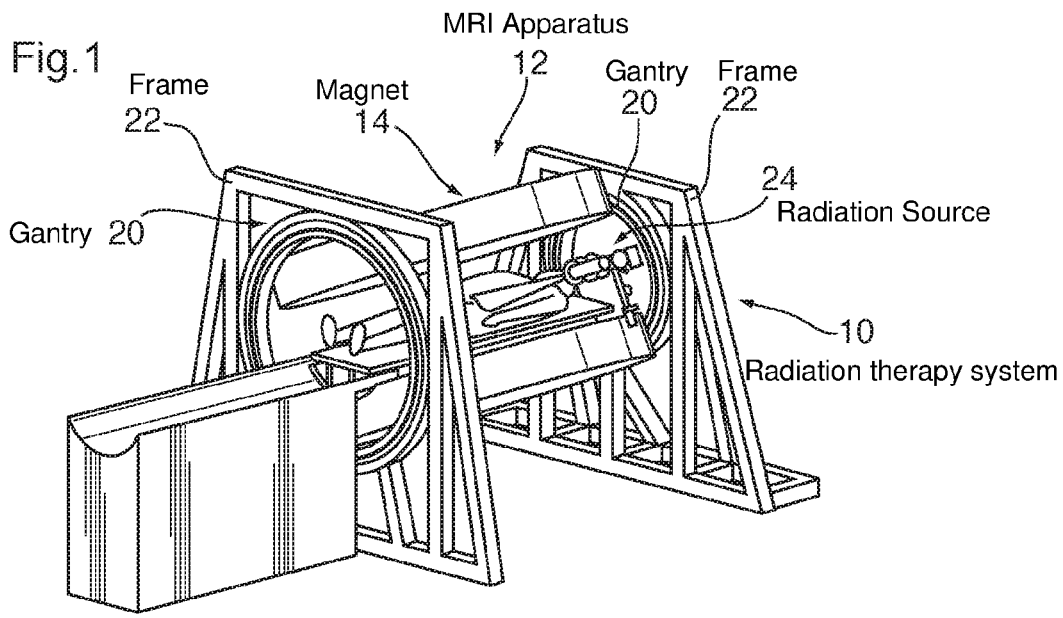
FIGS. 1 and 2 are perspective schematic views of image guided radiation therapy systems.
Figure 2:
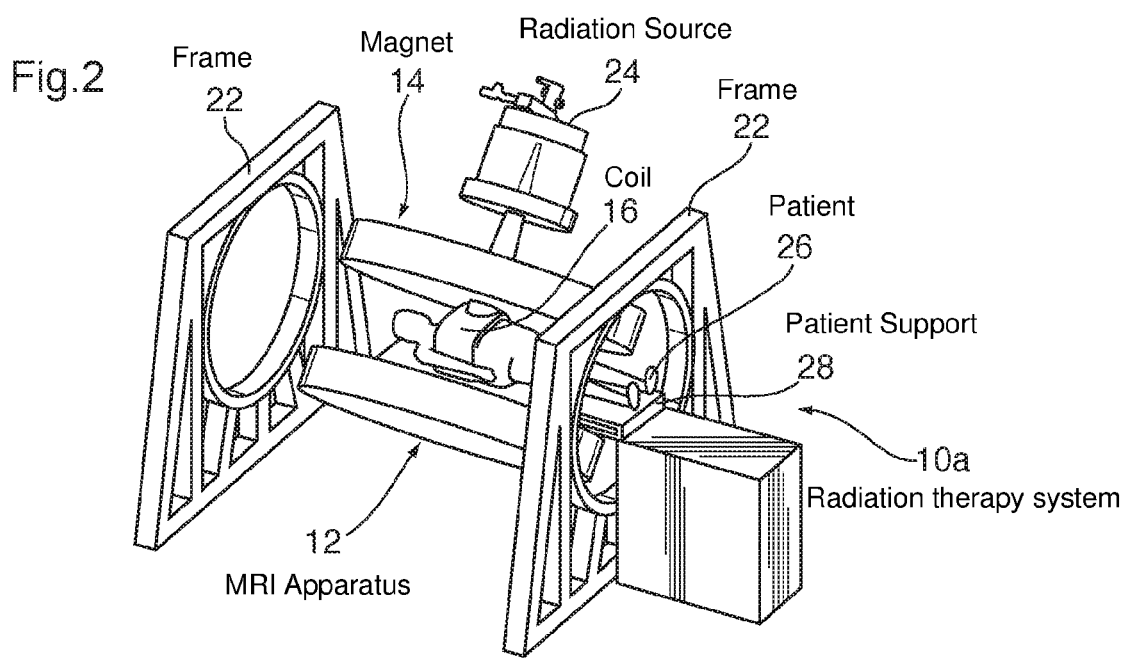

For convenience, like numerals in the description refer to like structures in the drawings. Referring to FIGS. 1 and 2 perspective schematic views of a radiation therapy system are illustrated generally by numeral 10. The radiation therapy system 10 includes an MRI apparatus 12, a radiation source 24, rotational gantries 20, a patient support 28 and a processing structure (not shown). In this embodiment, the processing structure is located near a console of the radiation therapy system 10, which is outside of the treatment room. The MRI apparatus 12 comprises a split solenoid magnet 14 and an RF detector coil 16. In this embodiment, the radiation source 24 comprises a linear accelerator (linac). The rotational gantries 20 are rotatable coupled to a respective frame 22. The RF detector coil 16 is configured to be positioned about a patient 26 on the patient support 28. The split solenoid magnet 14 is mounted on the rotational gantries 20. The processing structure in configured to process data received by the RF detector coil 16.

It is possible to configure the linac 24 in a parallel configuration or a perpendicular configuration. For example, a parallel configuration is illustrated in FIG. 2. Specifically, the linac 24 is positioned to direct a radiation treatment beam in a direction parallel to magnetic field lines of the split solenoid magnet 14 for treatment of the patient 26. A perpendicular configuration is illustrated in FIG. 1. Specifically, the linac 24 is positioned to direct a radiation treatment beam perpendicular to the magnetic field lines of the split solenoid magnet 14. Regardless of the configuration, the position of the radiation treatment beam with respect to the split solenoid magnet 14 is fixed such that the linac 24 rotates around the patient 26 with the split solenoid magnet 14, or is maintained in a fixed position with the split solenoid magnet 14 while the patient is rotated.

Referring to FIG. 3, a schematic view of a radiation treatment beam 18 and the RF detector coil 16 is shown. As shown, the radiation treatment beam 18 generated by the linac 24 can be incident on RF detector coil 16 of the MRI apparatus 12 during treatment and imaging.

MRI raw data received at the processing structure from the RF detector coil 16 is represented in k-space. K-space refers to a data matrix containing raw image information collected by the MRI apparatus 12. In two-dimensional k-space, the row location of the values in the data matrix is determined by a range of phase values, and the columns of the matrix corresponding to the range of frequency values. The pixel values in the k-space corresponds to the Fourier transform of the distribution of the density of protons in MRI images generally weighted according to the relaxation of the tissue types.

One horizontal line of the k-space data, represents data collected during one need cycle of the MRI apparatus 12. Generally, the phase gradient while being fixed for one line of k-space varies among the k-space lines, and the read gradient encodes the location of the tissue in directions orthogonal to the phase encoding gradient by 1-2-1 assignment of a frequency to each location. The relationship between the k-space data and the final MRI Image is the Fourier Transform. Thus, a Fourier Transform of the k-space data will yield a spatial MRI image in which the spatial features of the target and surrounding volumes can be seen. The directions of the k-space data, i.e. the matrix size (e.g. 256×128), are typically identical to the matrix size of the final MRI image generated from the k-space data.

Figure 4A:
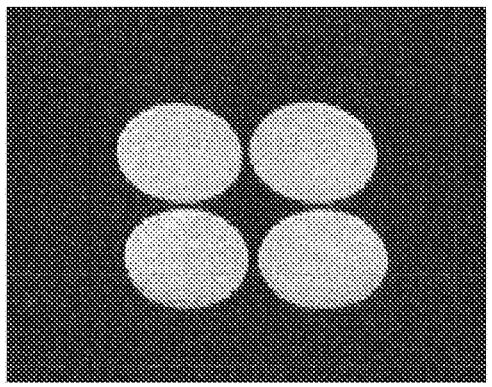
FIGS. 4a and 4b are MRI images obtained with a radiation treatment beam inactive and active, respectively.
Figure 4B:
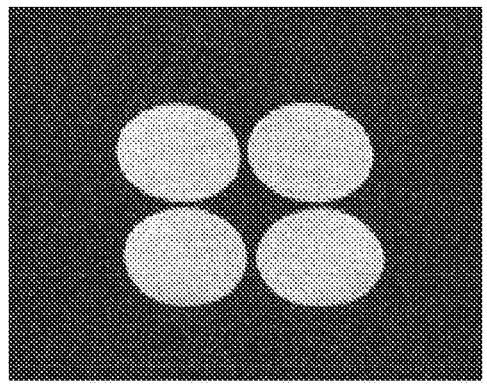
Figure 5A:
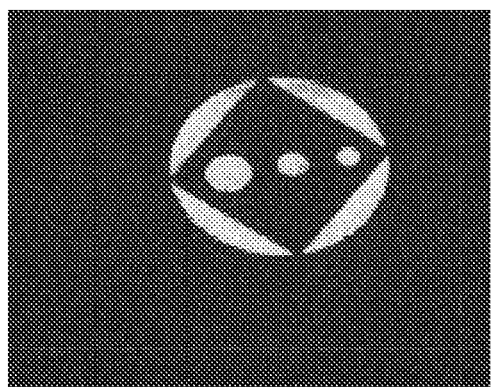
FIGS. 5a and 5b are additional MRI images obtained with a radiation treatment beam inactive and active, respectively.
Figure 5B:
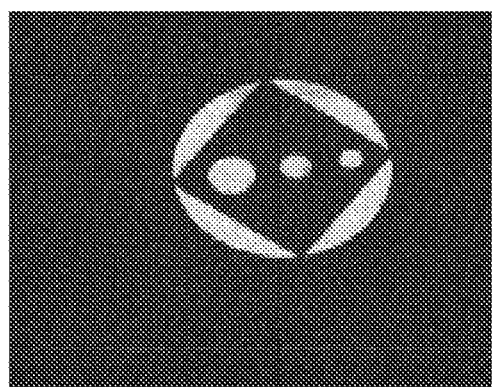

Referring to FIGS. 4a and 5a clear of MRI images are illustrated. That is, the MRI images shown in FIGS. 4a and 5a were obtained when the linac 24 was not active. Referring to FIGS. 4b and 5b, MRI images affected by the radiation induced current are illustrated. That is, the MRI images shown in FIGS. 4b and 5b were obtained when the linac 24 was active. For these examples, the imaging repetition time of the MRI apparatus 12 is 300 ms and the radiation treatment beam is generated by the linac 24 at a 250 monitor unit per minute (MU/min) dose rate. Monitor unit (MU) is a measure of dose delivered by the linac 24, standardized to a measurement in water. As shown in FIGS. 4 and 5, the effect of radiation induced current is not visible to the naked eye. However, as will be described, a loss of signal-to-noise ratio (SNR) can be measured.

Further, it was discovered that visual artefacts, as a result of the radiation induced currents, are present in k-space, prior to creation of the MRI image. Referring to FIG. 6, a k-space image without the radiation treatment beam the incident on the RF coil 16 is shown. For sake of clarity, a k-space image refers to a visual representation of the k-space data as is known in the art. As shown, the k-space image generally comprises a bright signal region near the centre and dark background regions near the corners.

Referring to FIG. 7, an example of a k-space image with the radiation treatment beam incident on the RF coil 16 is shown. As can be seen, visual artefacts can be seen in the image. In this example, the visual artefacts are substantially vertical, parallel lines. The number of visual artefacts is based, at least in part on the dose rate of the linac 24.

The linac 24 nominally outputs pulses of the radiation treatment beam at 180 Hz or approximately one pulse every 5.6 ms. The linac pulse rate is different from the linac dose rate, which is a measure of the dose received by the patient averaged over a minute. Thus, assuming that the linac 24 pulses at each 5.6 ms interval, an artefact will appear in the k-space data every 5.6 ms during a single read cycle of the MRI apparatus 12. However, in order to achieve the desired dose rate, the linac 24 may drop some of the pulses. That is, the linac 24 may not transmit a pulse at one or more given cycles, resulting in fewer pulses than one every 5.6 ms. Accordingly, decreasing the linac dose rate will generally decrease the number of pulses during a single read cycle and thus, increase the space between artefacts in the k-space images resulting in fewer image artefacts in a single read cycle. For example, the number of pulses at 250 MU/min is five (5) times the number of pulses at 50 MU/min and thus, creates five (5) times the number of artefacts in the k-space data during a single read cycle of the MRI apparatus 12. The increased number of artefacts in the k-space data results in an increase in overall image noise, and conversely, a decreased SNR. Thus, without any processing of the k-space data, a decrease in the dose rate of the linac improves the SNR of the k-space data.

Further, the manifestation of the visual artefacts a k-space image may vary depending on the imaging repetition time of the MRI apparatus 12. The imaging repetition time of the Mill apparatus 12 used to obtain the image illustrated in FIG. 7 is 300 ms. Referring to FIG. 8, another example of a k-space image with the radiation treatment beam incident on the RF coil 16 is shown. The imaging repetition time of the MM apparatus 12 used to obtain this image is 300.1 ms. In this example, the visual artefacts are substantially diagonal, parallel lines. Referring to FIG. 9, yet another example of a k-space image with the radiation treatment beam incident on the RF coil 16 is shown. The imaging repetition time of the Mill apparatus 12 used to obtain this image is 301 ms. In this example, the visual artefacts appear as random background noise. As can be seen, even a relative small change of 0.1 ms in the imaging repetition time can affect how the radiation induce current is represented in k-space.

The processing structure is configured to provide processing software to mitigate the effect of the radiation induced current. Specifically, the processing software is configured to process the raw MRI data in k-space to reduce the artefacts created by the radiation induced current.

The processing software is configured to identify a plurality of points in k-space that have been corrupted by the radiation induced current. This is achieved by comparing an intensity of each of the pixels in the k-space image with the global threshold. If the pixel intensity is less than the global threshold, then the pixel likely belongs to an uncorrupted background portion of the k-space image. If the pixel intensity is greater than the global threshold, then the pixel intensity may be corrupted and may need to be corrected. In this embodiment, the pixel intensity is corrected if it is determined that the pixel lies away from the signal region in the k-space image. The pixel is corrected by changing its intensity value to represent a background pixel. A resulting, modified k-space image is used to generate the MRI image, which will have an improved SNR. An algorithm implemented by the processing software is described below.

Figure 12:
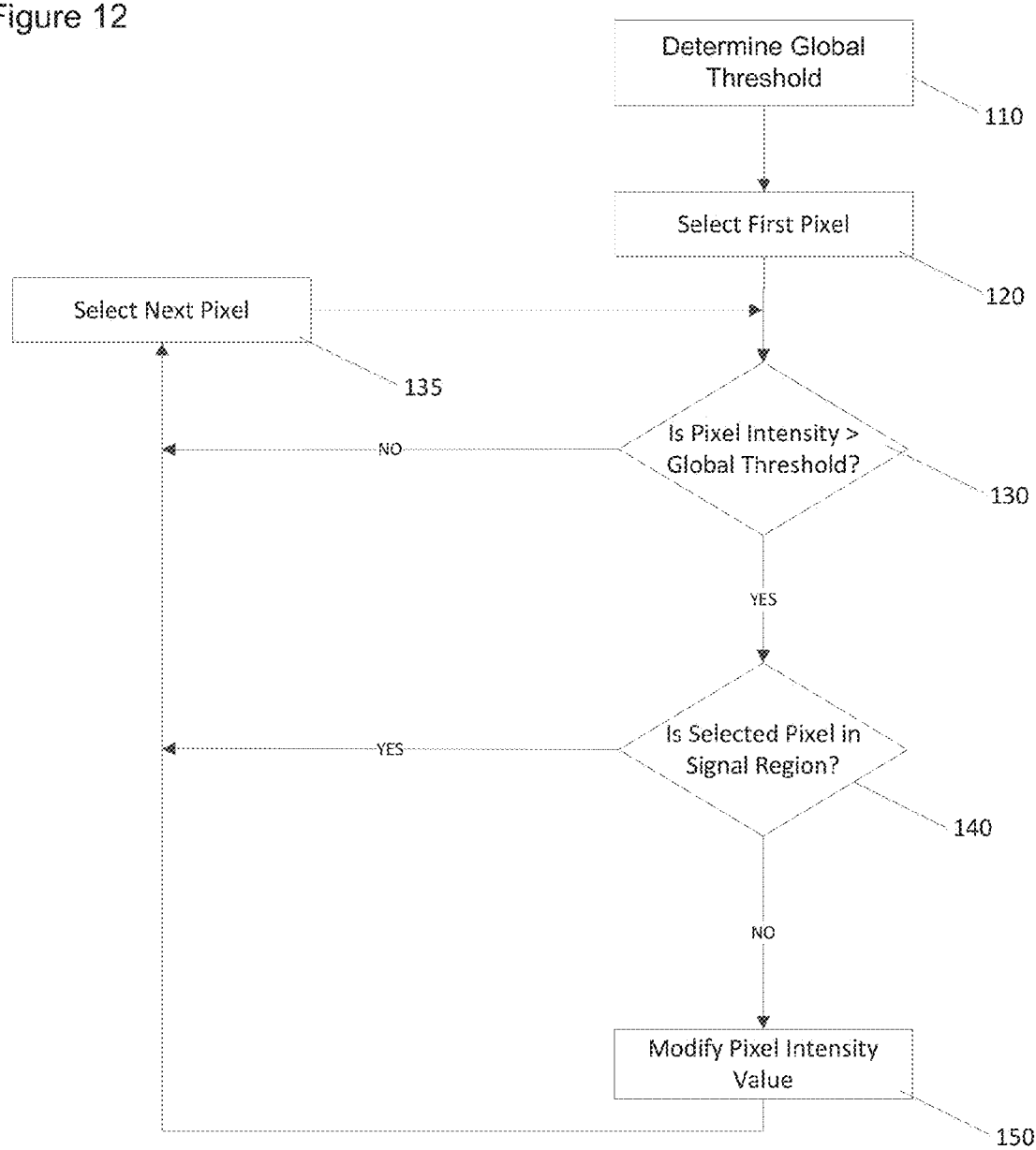
FIG. 12 is a flowchart showing steps for identifying and reducing artefacts in k-space image that are likely caused by radiation induced current.

Referring to FIG. 12, a flowchart illustrating steps for reducing the effect of radiation induced current on MRI images is shown generally by numeral 1200. The steps are applied to the k-space image, prior to generating the MRI image.

At step 110, the global threshold is determined. In this embodiment, the global threshold is based on an average and standard deviation of background pixel intensity for the k-space image. In this embodiment, the average and standard deviation of background pixel intensity is determined by analysing pixels at the corners of the k-space image. As previously noted, and can be seen in FIGS. 6 to 9, the corners of the k-space image primarily comprise background pixels. Average and standard deviation of the pixel intensity for these pixels can be determined using known algorithms. The number of pixels selected from the corners of the k-space image can be varied based on the size of the image acquired. The pixels can be selected from one, two, three or all four corners of the k-space image, depending on the implementation. The global threshold is then defined as the average background pixel intensity plus three standard deviations of the background pixel intensity.

At step 120, a first pixel in the k-space image is selected. At step 130, the pixel intensity for the selected pixel is compared with the global threshold. If the pixel intensity for the selected pixel is less that the global threshold, then the pixel likely represents an uncorrupted background pixel and the processing software continues at step 135. At step 135, a next pixel is selected and the processing software continues at step 130.

Returning to step 120, if, however, the pixel intensity for the selected pixel is greater that the global threshold, then the selected pixel may represent a corrupted background pixel and the processing software continues at step 140. At step 140, the selected pixel is analysed to determine if it lies within the signal region of the k-space image. As will be appreciated, any artefacts within the signal region will likely have a minimal effect on the SNR because they are sparsely distributed compared to the MRI signal. Further, the magnitude of the artefacts will likely be relatively small in comparison to the MRI signal. Accordingly, if it is determined that the selected pixel lies within the signal region of the k-space image, then the selected pixel is not modified and the processing software continues at step 135.

If, however, it is determined that the selected pixel lies outside of the signal region of the k-space image, then the processing software continues at step 150. At step 150, the pixel intensity of the selected pixel is modified to a value that is equal to the average background value, as determined in step 110. In this way, the effect of the artefact is reduced in the k-space image. The processing software continues at step 135.

In this embodiment, the processing software continues until all pixels in the k-space image have been selected and processed as described above. However, in an alternate embodiment, only a subset of the pixels in the k-space image may be processed as described above, while still achieving a substantial reduction or elimination of artefacts. For example, one implementation may involve processing only every other row of the k-space image, or every other column of the k-space image, or processing only those pixels outside of a central region of the k-space image.

Figure 13A:
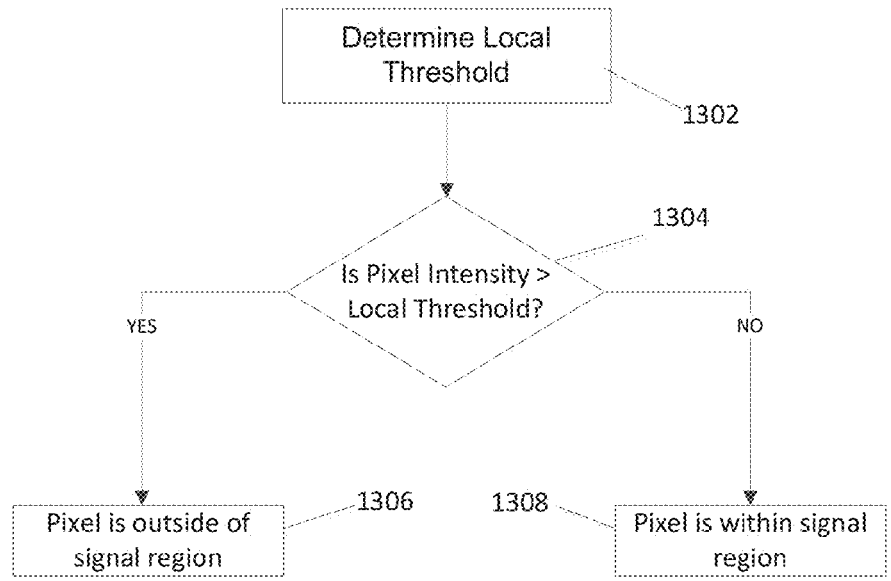
FIG. 13a is a flowchart illustrating steps for determining whether a selected pixel is within a signal region of the k-space image in accordance with an embodiment.

Referring to FIG. 13a, an algorithm for determining if a selected pixel lies within the signal region of the k-space image in accordance with one embodiment is illustrated. In this embodiment, neighboring pixels are used to determine if the selected pixel lies within the signal region of the k-space image. At step 1302, a local threshold is determined. In this embodiment, the local threshold is based on an average and standard deviation of a local average pixel intensity. In this embodiment, the local average pixel intensity is determined based on a 5×5 square of pixels centred on the selected pixel. However, other matrix sizes may be used. For the first and last two rows/columns of pixels, the local average pixel intensity is determined based on a portion of the 5×5 square which is available. For example, for a pixel in the top row, the local average pixel intensity is determined based on two pixels to the left of the selected pixel, two pixels to the right of the selected pixel, and two rows of five pixels below the selected pixel. A standard deviation for the local average pixel intensity is also determined. The local threshold is determined as the local average pixel intensity plus three standard deviations. At step 1304, the pixel intensity of the selected pixel is compared with the local threshold. If the selected pixel intensity is greater than the local threshold, then, at step 1306, the selected pixel is determined to be outside the signal region of the k-space image. If the selected pixel intensity is less than the local threshold, then, at step 1308, the selected pixel is determined to be within signal region of the k-space image.

For this embodiment, in step 150, it is possible to modify the pixel intensity of the selected pixel to a value that is equal to the local average pixel intensity rather than modify the pixel intensity of the selected pixel to a value that is equal to the average background value.

Figure 13B:
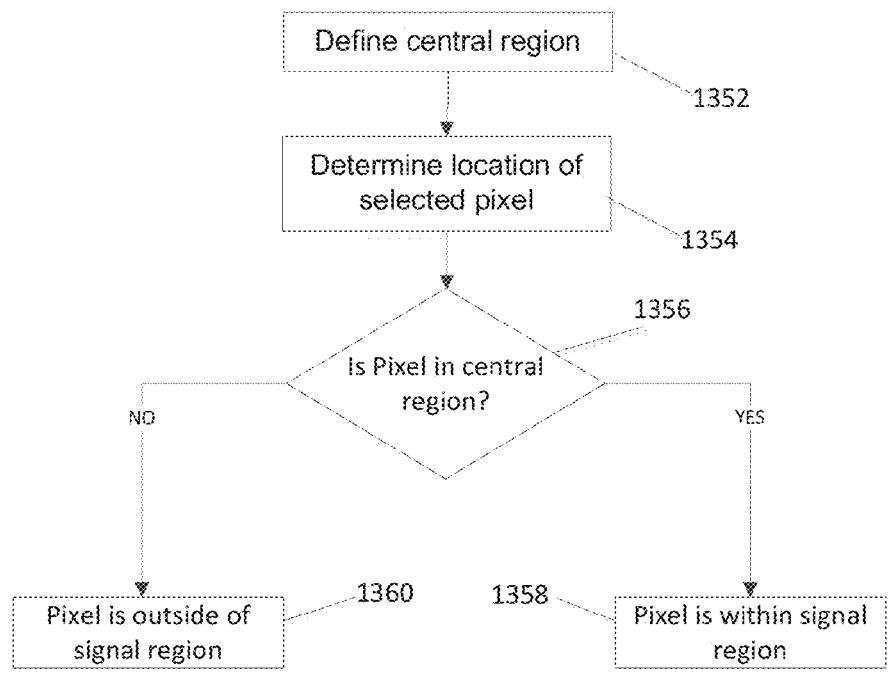
FIG. 13b is a flowchart illustrating steps for determining whether a selected pixel is within a signal region of the k-space image in accordance with an alternate embodiment.

Referring to FIG. 13b, an algorithm for determining if a selected pixel lies within the signal region of the k-space image in accordance with an alternate embodiment is illustrated. In accordance with this embodiment, a geographic method is used to predefine a region considered to be the 'signal region'. At step 1352 a central region is defined. Specifically, for a k-space image having a pixel resolution of [M×N], a central region of pixels, smaller than [M×N], containing the majority of the MR signal is defined as the signal region. The central region may be determined by a user manually interfacing with a graphical user interface tool of the processing software. Specifically prior to analysis of the k-space image, the graphical user interface of the processing software presents the k-space image on a display and receives input via a user input device defining the central region. Alternatively, pattern recognition software may be used to automatically define the central region. At step 1354, the processing software determines the location of the selected pixel. At step 1356, the processing software determines whether the selected pixel is physically positioned within the central region. If it is determined that the selected pixel is within the central region, then, at step 1358, the selected pixel is determined to be within the signal region of the k-space image. If it is determined that the selected pixel is positioned outside of the central region, then, at step 1360, the selected pixel is determined to be outside of the signal region of the k-space image.

While the above has been described in terms of modifying the pixel value in the k-space image, it will be understood that a new k-space image can be created based on the original k-space image and the above-described process so that the original k-space image is not destroyed.

Further, while the global threshold has been described above as the average background pixel intensity plus three standard deviations of the background pixel intensity, the determination of the global threshold may vary. For example, the global threshold may be determined as the average background pixel intensity plus two standard deviations of the background pixel intensity. As another example, the global threshold may be determined as the average background pixel intensity plus four standard deviations of the background pixel intensity. As yet another example, the global threshold may be determined as the average background pixel intensity plus a particular percentage. The local threshold may similarly vary depending on the implementation.

As will be appreciated, the processing software may be implemented after the k-space images have been acquired or while the k-space images are being acquired.

Referring to FIGS. 10a and 10b, the effects of the processing software are shown. FIG. 10a illustrates the k-space image received from the MRI apparatus 12 and FIG. 10b illustrates the k-space image after processing by the processing software. As can be seen, the near vertical line artefacts in FIG. 10a, caused by the radiation induced current, are absent in FIG. 10b.

As previously described, the artefacts caused by the radiation induced current may not be apparent to the naked eye in the MRI images. However, the effects of the radiation induced current are apparent when the system SNR is examined. A comparison of different SNR results for different linac dose rates are provided in Table 1, below. The data in Table 1 was collected using a 10 cm MRI RF detector coil 16 and the SNR was calculated by taking the mean value of regions containing signal in the MRI image and dividing this by the standard deviation of the background noise.

TABLE 1

| Linac Dose Rate (MU/min) | SNR with Linac Radiation Treatment Beam Blocked by Lead Block | SNR with Linac Radiation Treatment Beam Incident upon MRI RF Detector Coil | SNR after Processing of the k-space Image |
|---|---|---|---|
| 0 | 18.2 ± 0.2 | — | — |
| 50 | 18.0 ± 0.4 | 17.7 ± 0.1 | 17.9 ± 0.1 |
| 100 | 17.8 ± 0.3 | 17.4 ± 0.3 | 17.8 ± 0.2 |
| 150 | 18.2 ± 0.3 | 16.9 ± 0.2 | 17.3 ± 0.2 |
| 200 | 17.8 ± 0.1 | 16.5 ± 0.2 | 17.2 ± 0.3 |
| 250 | 17.8 ± 0.1 | 16.2 ± 0.3 | 17.0 ± 0.5 |

Figure 11A:
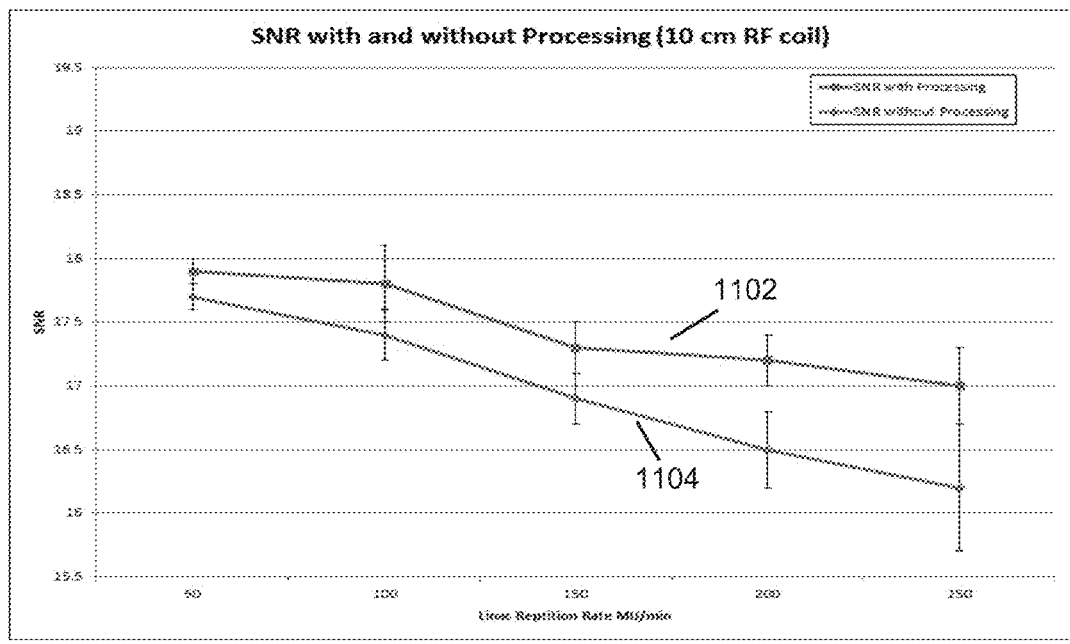
FIG. 11a is a graph showing SNR in signals obtained with a 10 cm RF detector coil with and without processing of the k-space image.

The data in Table 1 is plotted in the graph shown in FIG. 11a. As will be appreciated, the SNR 1102 for the MRI image processed by the processing software is significantly improved compared to the SNR 1104 for the non-processed MRI image.

A comparison of different SNR results for different linac dose rates are provided in Table 2, below. The data in Table 2 was collected using a 3 cm MRI RF detector coil 16.

TABLE 2

| Linac Dose Rate (MU/min) | SNR with Linac Radiation Treatment Beam Blocked by Lead Block | SNR with Linac Radiation Treatment Beam Incident upon MRI RF Detector Coil | SNR after Processing of the k-space Image |
|---|---|---|---|
| 0 | 19.7 ± 0.3 | — | — |
| 50 | 19.5 ± 0.4 | 18.7 ± 0.3 | 18.9 ± 0.3 |
| 100 | 19.5 ± 0.3 | 18.0 ± 0.3 | 18.7 ± 0.4 |
| 150 | 19.5 ± 0.4 | 17.7 ± 0.4 | 18.7 ± 0.3 |
| 200 | 19.3 ± 0.2 | 17.0 ± 0.1 | 18.3 ± 0.2 |
| 250 | 19.1 ± 0.4 | 16.9 ± 0.3 | 18.5 ± 0.3 |

Figure 11B:
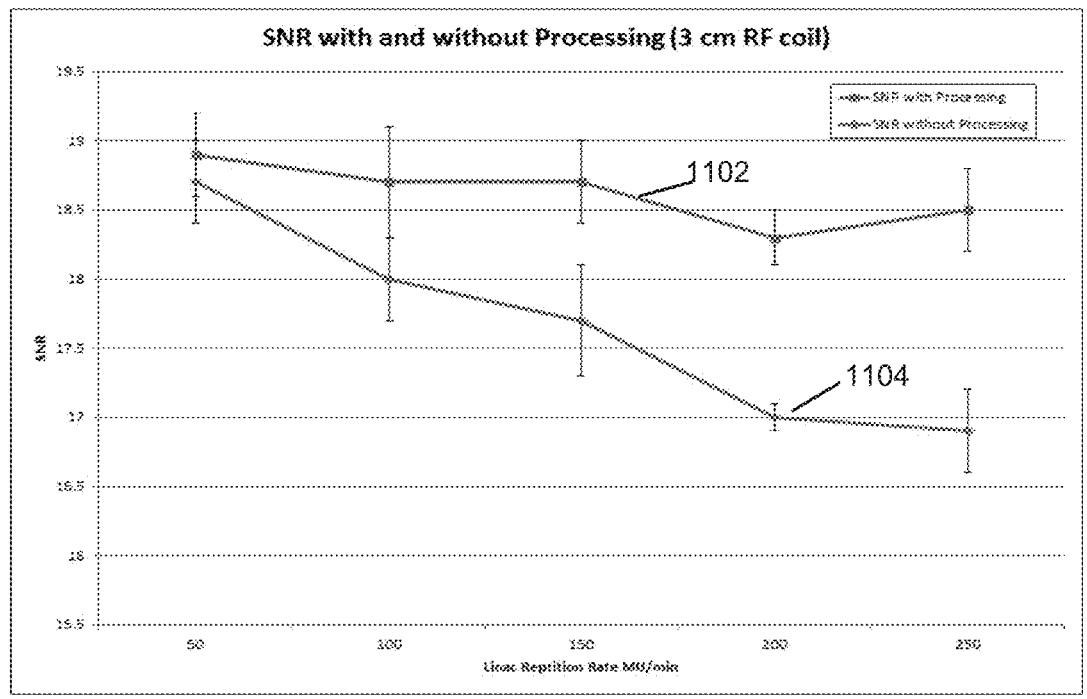
FIG. 11b is a graph showing the SNR in signals obtained with a 3 cm RF detector coil with and without processing of the k-space image.

The data in Table 2 is plotted in the graph shown in FIG. 11b. As will be appreciated, the SNR 1102 for the MRI image processed by the processing software is significantly improved compared to the SNR 1104 for the non-processed MRI image.

Using the foregoing specification, the invention may be implemented as a machine, process or article of manufacture by using standard programming and/or engineering techniques to produce programming software, firmware, hardware or any combination thereof.

Any resulting program(s), having computer-readable instructions, may be stored within one or more computer-usable media such as memory devices or transmitting devices, thereby making a computer program product or article of manufacture according to the invention. As such, the term "software" as used herein is intended to encompass a computer program existent as instructions on any non-transitory computer-readable medium such as on any memory device that are to be executed by a processor. Examples of memory devices include hard disk drives, diskettes, optical disks, magnetic tape, semiconductor memories such as FLASH, RAM, ROM, PROMS, and the like.

A machine embodying the invention may involve one or more processing systems including, for example, CPU, memory/storage devices, communication links, communication/transmitting devices, servers, I/O devices, or any subcomponents or individual parts of one or more processing systems, including software, firmware, hardware, or any combination or subcombination thereof, which embody the invention as set forth in the claims.

Using the description provided herein, those skilled in the art will be readily able to combine software created as described with appropriate general purpose or special purpose computer hardware to create a computer system and/or computer subcomponents embodying the invention, and to create a computer system and/or computer subcomponents for carrying out the method of the invention.

Although preferred embodiments of the invention have been described herein, it will be understood by those skilled in the art that variations may be made thereto without departing from the scope of the appended claims.

What is claimed is:

1. A computer-implemented method in order to reduce artefacts in an MRI image, the artefacts introduced as a result of radiation induced current when a radiation treatment beam of a radiation source is applied and incident on collector coils of an MRI apparatus, the method comprising:

simultaneously operating an MRI apparatus in order to obtain MRI image information of a patient and a radiation source in order to direct a radiation beam onto a patient;

selecting a plurality of pixels in k-space data obtained by the MRI apparatus during the step of simultaneously operating the MRI apparatus and the radiation source, wherein the step of selecting is performed prior to generation of an MRI image;

analyzing with a computer processor a pixel intensity of each of the plurality of selected pixels in order to determine whether a pixel intensity of each of the plurality of selected pixels is greater than a predefined global threshold;

wherein for each pixel having pixel intensity greater than the predefined global threshold, determining whether the pixel lies within a signal region of the k-space data or outside of the signal region of the k-space data;

wherein for each pixel that lies outside the signal region of the k-space data, automatically modifying the pixel intensity with a computer processor in order to be similar to a background pixel intensity, thereby modifying the k-space data; and after modifying the k-space data, then generating an MRI image based on the modified k-space data;

whereby the artefacts created by application of the radiation treatment beam that are incident on the collector coils are reduced in the generated MRI image.

2. The method of claim 1 wherein the background pixel intensity is determined by averaging the intensities of a plurality of background pixels in the k-space data.

3. The method of claim 2 wherein the plurality of background pixels are each selected from corners of the k-space data.

4. The method of claim 2 wherein the global threshold arises from the background pixel intensity plus a predefined deviation therefrom.

5. The method of claim 1, wherein the step of determining whether the selected pixel lies within the signal region of the k-space data or outside of the signal region of the k-space data comprises:

determining a local threshold based on a predefined matrix occurring around or nearby the selected pixel with the computer processor;

comparing the intensity of the selected pixel with the determined local threshold; and providing a result that the selected pixel is outside of the signal region of the k-space data when the intensity of the selected pixel is greater than the determined local threshold.

6. The method of claim 5 wherein the local threshold arises from an average pixel intensity of the predefined matrix plus a predefined deviation therefrom.

7. The method of claim 1, wherein determining whether the selected pixel lies within the signal region of the k-space data or outside of the signal region of the k-space data comprises:

defining with the computer processor a central region of the k-space data as the signal region;

comparing a location of the selected pixel with the central region of the k-space data; and determining that the selected pixel is outside of the signal region of the k-space data when the location of the selected pixel is physically outside of the central region.

8. The method of claim 7, wherein the central region of the k-space data is defined by a user selecting an array of pixels in the k-space data a graphical user interface.

9. The method of claim 7 wherein the background pixel intensity is determined as an average of the intensities of a plurality of pixels neighboring the selected pixel in the k-space data.

10. A non-transitory computer-readable medium having stored thereon instructions that when executed by a computing device reduces artefacts in an MRI image, where the artefacts were introduced as a result of radiation induced current when a radiation treatment beam generated by a radiation source is incident on collector coils of an MRI apparatus during simultaneous operation of the MRI apparatus and the radiation source, the instructions when executed by a processor cause the processor to:

select a plurality of pixels in a k-space data obtained by an MRI apparatus during simultaneous operation of the MRI apparatus and a radiation source prior to generation of the MRI image;

analyse each of the plurality of selected pixels in order to determine whether a pixel intensity is greater than a predefined global threshold;

for each pixel having pixel intensity greater than the predefined global threshold, determine whether the pixel lies within a signal region of the k-space data or outside of the signal region of the k-space data;

for each pixel that lies outside of the signal region, modify the pixel intensity to be similar to a background pixel intensity, thereby modifying the k-space data; and after modifying the k-space data, generate an MRI image based on the modified k-space data;

wherein the artefacts created by application of a radiation treatment beam from the radiation source are reduced in the generated MRI image.

11. The non-transitory computer readable medium of claim 10 wherein the background pixel intensity is determined by averaging the intensities of a plurality of background pixels in the k-space data.

12. The non-transitory computer readable medium of claim 11 wherein the plurality of background pixels are each selected from corners of the k-space data.

13. The non-transitory computer readable medium of claim 11 the global threshold arises from the background pixel intensity plus a predefined deviation therefrom.

14. The non-transitory computer readable medium of claim 10, wherein the instruction of determining whether the selected pixel lies within the signal region of the k-space data or outside of the signal region of the k-space data comprises instructions that:

determine a local threshold based on a predefined matrix occurring around or nearby the selected pixel with the computer processor;

compare the intensity of the selected pixel with the determined local threshold; and determine that the selected pixel is outside of the signal region of the k-space data when the intensity of the selected pixel is greater than the determined local threshold.

15. The non-transitory computer readable medium of claim 14 wherein the local threshold arises from an average pixel intensity of the predefined matrix plus a predefined deviation therefrom.

16. The non-transitory computer readable medium of claim 10, wherein the instructions that determine whether the selected pixel lies within the signal region of the k-space data or outside of the signal region of the k-space data comprises instructions to:

define with the computer processor a central region of the k-space data as the signal region;

compare a location of the selected pixel with the central region of the k-space data; and determine that the selected pixel is outside of the signal region of the k-space data when the location of the selected pixel is physically outside of the central region.

17. The non-transitory computer readable medium of claim 16, wherein the central region of the k-space data is defined by a user selecting an array of pixels in the k-space data a graphical user interface.

18. The non-transitory computer readable medium of claim 16 wherein the background pixel intensity is determined as an average of the intensities of a plurality of pixels neighboring the selected pixel in the k-space data.

19. The non-transitory computer readable medium of claim 10, wherein the modified k-space data is created separate from the k-space data.

20. A radiation therapy system comprising:

a radiation source that generates a radiation treatment beam;

a magnetic resonance imaging (MRI) apparatus that acquires image data using collector coils; and a computing device configured to process the acquired image data to reduce artefacts in an MRI image caused when the radiation treatment beam is incident on the collector coils of the MRI apparatus; the computing device comprising a processor and memory that stores instructions which, when executed, cause the processor to:

select a plurality of pixels in a k-space data obtained by the MRI apparatus during simultaneous operation of the MRI apparatus and the radiation source prior to generation of the MRI image;

analyze with the processor each of the plurality of selected pixels in order to determine whether a pixel intensity is greater than a predefined global threshold;

wherein for each pixel having pixel intensity greater than the predefined global threshold, determine whether the pixel lies within a signal region of the k-space data or outside of the signal region of the k-space data;

wherein for each pixel that lies outside of the signal region, modifying the pixel intensity of each pixel to be similar to a background pixel intensity, thereby modifying the k-space data; and after modifying the k-space data, generate an MRI image based on the modified k-space data;

wherein the artefacts created by application of the radiation treatment beam are reduced in the generated MRI image.

* * * * *